(12) United States Patent
Lerman (10) Patent No.: US 6,267,741 B1
(45) Date of Patent: Jul. 31, 2001

(54) CERVICAL THORACIC ORTHOSIS

(76) Inventor: Max Lerman, 1950 Carla Ridge, Beverly Hills, CA (US) 90210

( * ) Notice: Subject to any disclaimer, the term of this patent is extended or adjusted under 35 U.S.C. 154(b) by 0 days.

(21) Appl. No.: 09/571,637

(22) Filed: May 15, 2000

(51) Int. Cl.[7] .................................................. A61F 5/00
(52) U.S. Cl. ...................... 602/18; 602/19; 128/DIG. 23
(58) Field of Search .................... 128/845, 846, 128/DIG. 23; 602/17, 18, 19

(56) References Cited

U.S. PATENT DOCUMENTS

| | | | | |
|---|---|---|---|---|
| 4,628,913 | * | 12/1986 | Lerman | 602/19 |
| 5,201,702 | * | 4/1993 | Mars | 602/18 |
| 5,531,669 | * | 7/1996 | Varnau | 602/18 |
| 5,575,763 | * | 11/1996 | Nagata | 602/18 |

* cited by examiner

Primary Examiner—Michael A. Brown
(74) Attorney, Agent, or Firm—Christie, Parker & Hale, LLP (57) ABSTRACT

A cervical thoracic orthosis includes a chest plate and a back plate overlying a patient's chest and back, adjustable shoulder straps and waist straps for securing the chest and back plate to the patient's upper torso, an occipital support conforming to the shape of the patient's occipital region, an upright occipital support bar adjustably securing the occipital support to the back plate, a flexible chin support suspended inside a rigid chin support member, and an upright chin support bar adjustably securing the chin support member, to the chest plate. Axially rigid but bendable lateral support rods are fastened between the occipital support and the chin support member to provide a rigid surrounding frame structure that holds the patient's head in any fixed desired orientation. The lateral support rods are bendable to a desired configuration and releasably adjustable in length for shaping the rigid outer frame structure. The chin support member has a recessed region so that to the patient's chin is supported entirely by the flexible chin support without contacting the rigid chin support member while the sides of the chin support member apply a more rigid support to the jaw. A flexible forehead strap secured to the occipital support includes a non-skid skin adhesion material to enhance frictional contact with the patient's forehead for resisting movement of the patient's head even in the temporary absence of the chin support.

20 Claims, 5 Drawing Sheets

CERVICAL THORACIC ORTHOSIS

FIELD OF THE INVENTION

This invention relates to a cervical thoracic orthosis for use in immobilizing the head and neck region of a patient, particularly one who has had an upper spinal cord fracture.

BACKGROUND

A cervical injury, such as a fracture to the upper cervical spine, requires immobilization of the head, neck and sternum so that the upper cervical spine does not move. There is a need for an orthosis that immobilizes the head and neck of the patient, particularly when the patient is lying in a hospital bed. There is also a need to ensure that adjustments can be made to immobilize the patient's head in a desired position. In the past, braces used for immobilizing spinal fractures have not provided a truly effective means of preventing rotation of the patient's head or providing adjustments to the position in which the head is immobilized. My U.S. Pat. No. 4,628,913 discloses a cervical thoracic orthosis for maintaining the patient's upper cervical spine immobilized, for preventing undesired rotation of the patient's head, while also securely yet comfortably maintaining the patient's head in a desired angular position during immobilization. However, immobilization of the patient's head, neck and jaw regions is not completely effective inasmuch as some movements are still possible. In addition, it has been discovered that a continuous rigid support to the patient's chin can produce injury to the chin bone, and that added padding does not help and, in fact, makes the problem worse. Further, prior art cervical thoracic orthoses are not known to provide good immobilization for the patient's head if there is a need to temporarily remove the chin support while the patient is eating, for example.

The present invention provides a cervical thoracic orthosis which improves upon maintaining the patient's upper cervical spine completely immobilized while preventing undesired rotation of the patient's head. The invention also provides a chin support which prevents undue pressure on the patient's chin bone and at the same time allows for a temporary release of the chin support to facilitate sufficient jaw movement during eating while still maintaining immobilization of the patient's head.

SUMMARY OF THE INVENTION

Briefly, the cervical thoracic orthosis of this invention includes a chest plate for overlying the chest region of a patient, a back plate for overlying the back of the patient, and fasteners for securing the chest plate and back plate in a fixed position around the front and back sides of the patient's upper torso. A chin support secured to the chest plate holds the chin of the patient in a fixed position. An occipital support secured to the back plate holds the occipital portion of the patient's head in a fixed position.

In one embodiment of the invention, axially rigid but bendable lateral support members are fastened between and cooperate with the occipital support and the chin support to form a rigid frame structure surrounding the sides of the patient's neck region and the patient's jaw. A flexible forehead strap secured to the occipital support and adjustable for fastening around the patient's forehead provides sufficient support to preclude movement of the patient's head. The forehead strap in one embodiment is made from a skin adhesion material to enhance frictional contact with the patient's head to prevent slippage sufficiently for resisting movement of the patient's head even in the temporary absence of the chin support.

In another embodiment of the invention, the chin support comprises a flexible chin support, and a rigid chin support member affixed to a chin support bar that rigidly mounts to the front of the chest plate. The flexible chin support is adjustably suspended inside the chin support member to apply supporting pressure directly to the sides of the patient's jaw while the flexible chin support provides the sole means of support for the chin above a recessed front, central region of the chin support member. The recessed region of the chin support member provides an open space absent any means of applying rigid pressure contact to the underside of the patient's chin bone.

These and other aspects of the invention will be more fully understood by referring to the following detailed description and the accompanying drawings.

DETAILED DESCRIPTION

Figure 1:
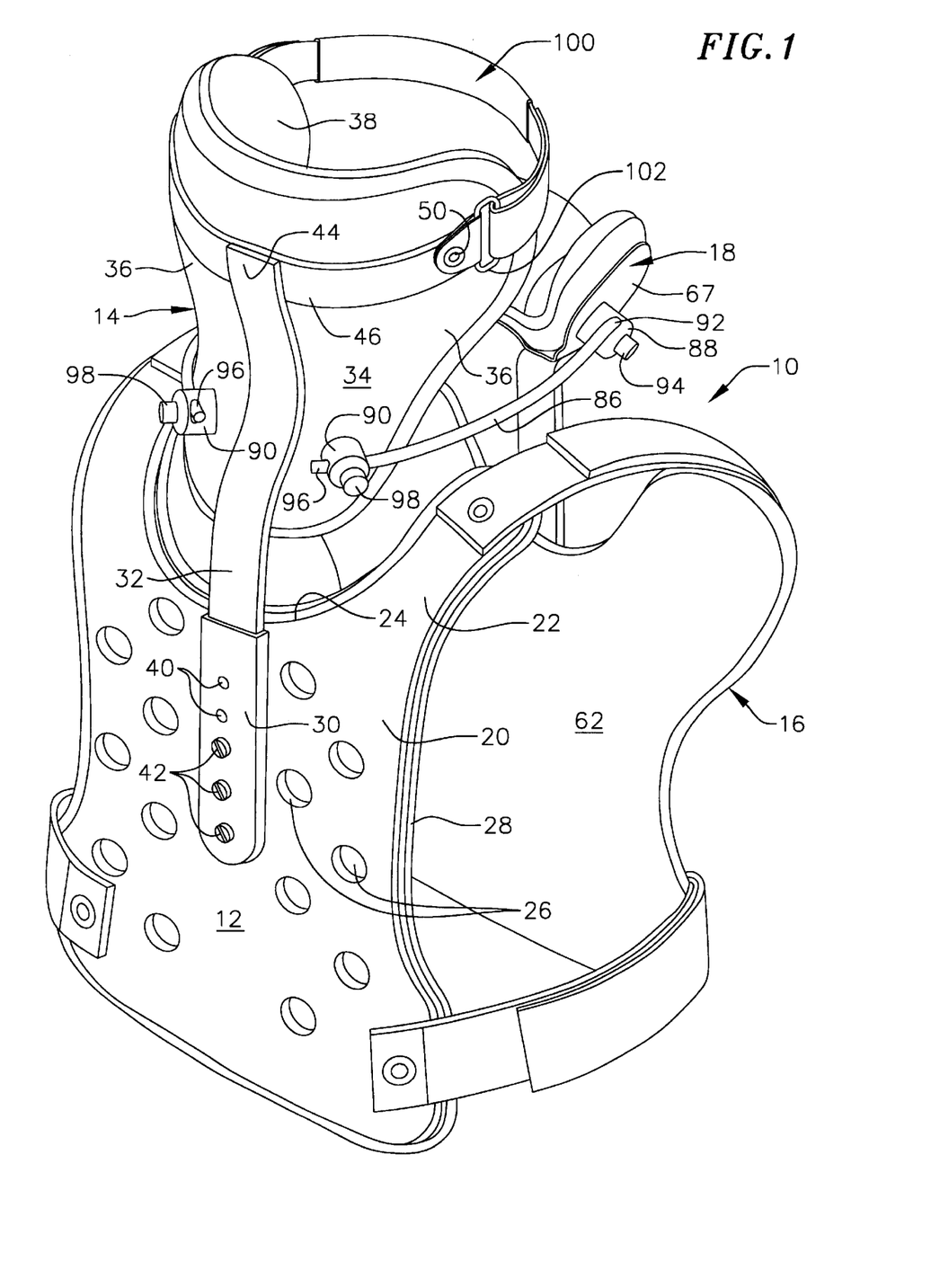
FIG. 1 is a perspective view showing front and rear portions of a cervical thoracic orthosis according to principles of this invention.

FIG. 1 is a perspective view showing a cervical thoracic orthosis 10 according to principles of this invention. The orthosis is secured around the patient for holding the patient's head, neck and upper torso in a fixed position to immobilize the patient's upper cervical spine. The orthosis includes a back plate 12 for overlying the upper region of the patient's back. The back plate holds an occipital support under the occipital region of the patient's head. A chest plate overlies the patient's sternum. The chest plate holds a chin support under the patient's chin.

Figure 2:
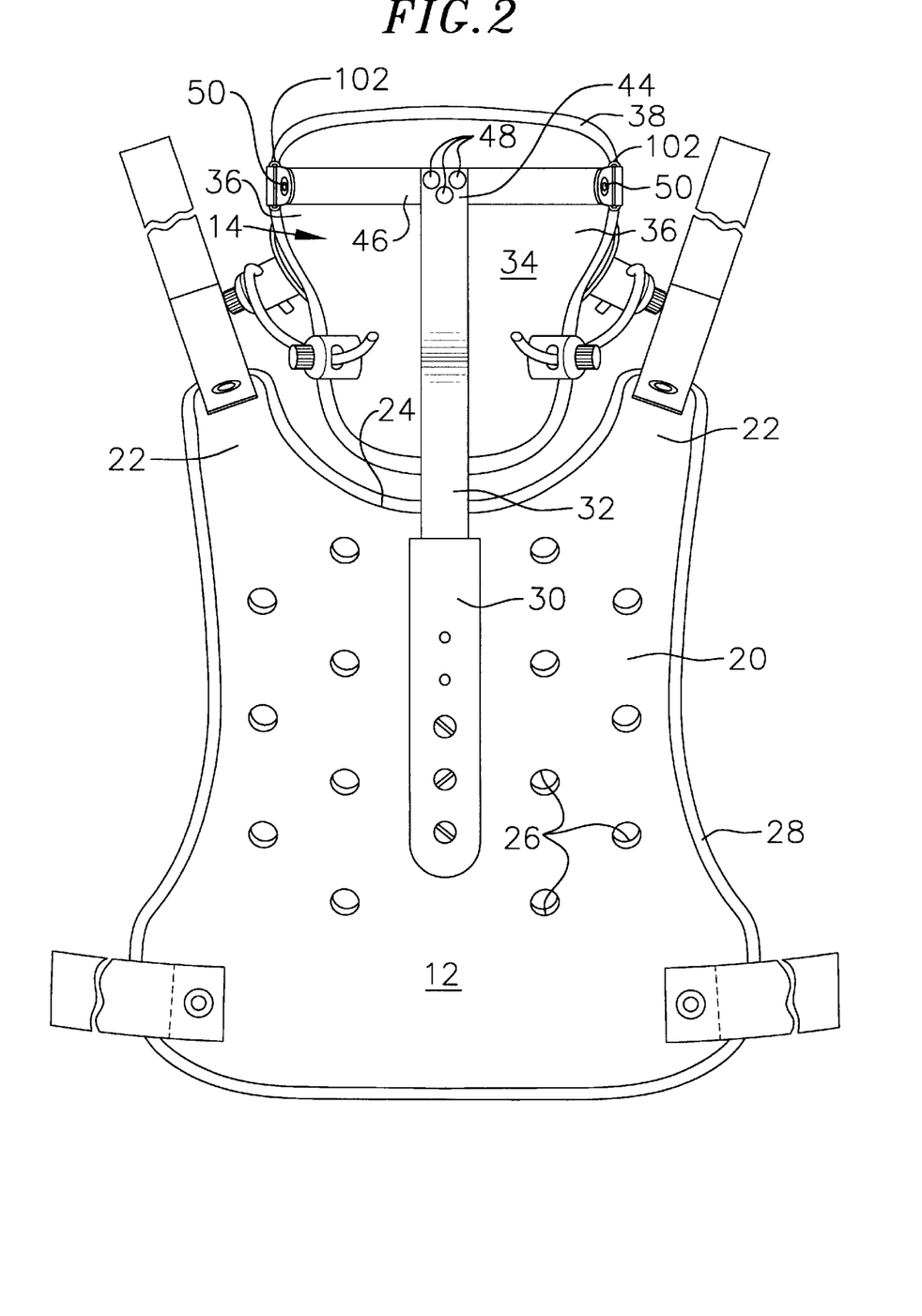
FIG. 2 is a fragmentary rear elevational view showing a back plate and an occipital support.

Construction of the back plate and the occipital support are understood best by referring to FIG. 2 in conjunction with FIG. 1. The back plate includes a semi-rigid self-supporting shell 20 made from a material preformed to an anatomical shape to overlie the upper portion of the patient's back. The shell extends across the width of the patient's back and the length of the shell extends from about the small of the patient's back upwardly to a pair of left and right upper extensions that overlie left and right rear portions of the patient's shoulder blades, respectively. The upper central portion of the shell has a U-shaped recess 24 that extends below the patient's upper cervical spine. The shell is preferably made from a thin sheet of polyethylene that is sufficiently flexible to be vacuum formed into the desired shape and which remains reasonably flexible after shaping. Air holes 26 are left in the shell to improve air circulation during use.

A layer of padding 28 covers the inside face of the shell. The layer preferably comprises an internal layer of an open cell resilient plastic foam material such as polyurethane foam used because it is breathable. The open cell foam layer is enclosed within an outer layer of a soft flexible fabric which is also breathable and preferably comprises velour. The resulting padding is affixed to the inside face of the shell by friction fasteners or a suitable adhesive. In the embodiment in which friction fasteners are used, the velour is releasably attached to a pair of upright friction fasteners (not shown) of the hook type affixed to the inside face of the shell on opposite of the sides of the receptacle.

A narrow, elongated, upwardly opening receptacle 30 is formed along the center of the back plate. The receptacle is integrally formed with the wall of the shell. The receptacle is formed during a vacuum forming process by placing a long, narrow insert in the mold and forming the outer wall of the receptacle from the same material as the outer wall of the shell. The insert is then removed, leaving the receptacle as a long, narrow projection of low profile with an opening at its top. The inner layer of padding forms an inside face adjacent the receptacle.

The receptacle receives the lower end of a rigid occipital support bar 32 component of the occipital support 14. The bar 32 supports an occipital support pad which includes a thin semi-rigid shell 34 preformed to the anatomical shape of the rear portion of the patient's head and the rear of the patient's neck. A lower portion of the shell overlies the rear portion of the patient's neck and the shell tapers wider an extends outwardly to form a cup-shaped upper region for overlying and conforming to the contour of the occipital region of the patient's head. The upper portion of the occipital support shell flares outwardly to form left and right upper sections 36 that extend around the left and right rear sides of the patient's head generally above the occipital region of the head. The shell 34 is made from the same type of thin sheet vacuum formable material such as polyethylene from which the shell of the back plate is made. In addition, the inside face of the occipital support has a layer of open cell foam padding 38 covered with velour similar to the padding on the inside face of the shell for the back plate. The padding 38 is secured to the inside face of the shell 34 by suitable friction fasteners.

A series of vertically spaced apart holes 40 are formed in the outer wall of the receptacle 30 on the back plate. A corresponding set of holes with the same spacing extend through the lower portion of the occipital support bar 32. The bar 32 is made from a metal such as aluminum. The lower portion of the bar is rigid but the upper portion is annealed to make the bar more bendable than the lower portion of the bar. The bar is inserted into the receptacle 30 and moved to the proper height adjustment for the occipital support. The holes in the bar are threaded internally, and the bar is held in a fixed position by aligning the holes in the bar with corresponding holes 40 in the receptacle, after which fasteners 42 are inserted into the holes 40 in the receptacle 30 and threaded into the holes in the bar 32 for holding the occipital support 14 in place. The upper portion of the bar 32 is bent inwardly to conform to the contour of the patient's neck. The bar is then bent outwardly near its bottom to conform to the shape of the occipital region of the patient's head. An upper end 44 of the bar terminates in the vicinity of the occipital region. The upper portion of the bar 32 which extends above the recess 24 in the back plate 20 conforms closely to the contour of the upper cervical spine to provide a rigid means of support along the upper cervical spine. The lower portion of the bar 32 provides a rigid means of support along the patient's spinal column below the patient's neck.

A generally U-shaped elongated metal lateral support bar 46 of narrow profile extends generally horizontally from left to right across the cup-shaped region of the occipital supporting shell 34. The lateral bar 46 is rigidly affixed at its center to the upper end 44 of the occipital support bar 32 by fasteners 48. These fasteners extend through the center of the lateral bar and the upper end of the occipital support bar and through the shell 36, rigidly fastening both bars to the center rear portion of the shell. Rivets 50 at opposite ends of the lateral support bar 46 extend through the bar and through the shell for affixing the ends of the bar to the upper outer sections of shell. The lateral support bar 46 in use provides a means of rigid support across the occipital region of the patient's head, extending from the vicinity behind one ear across the occipital region to the vicinity behind the ear on the opposite side of the patient's head.

Figure 3:
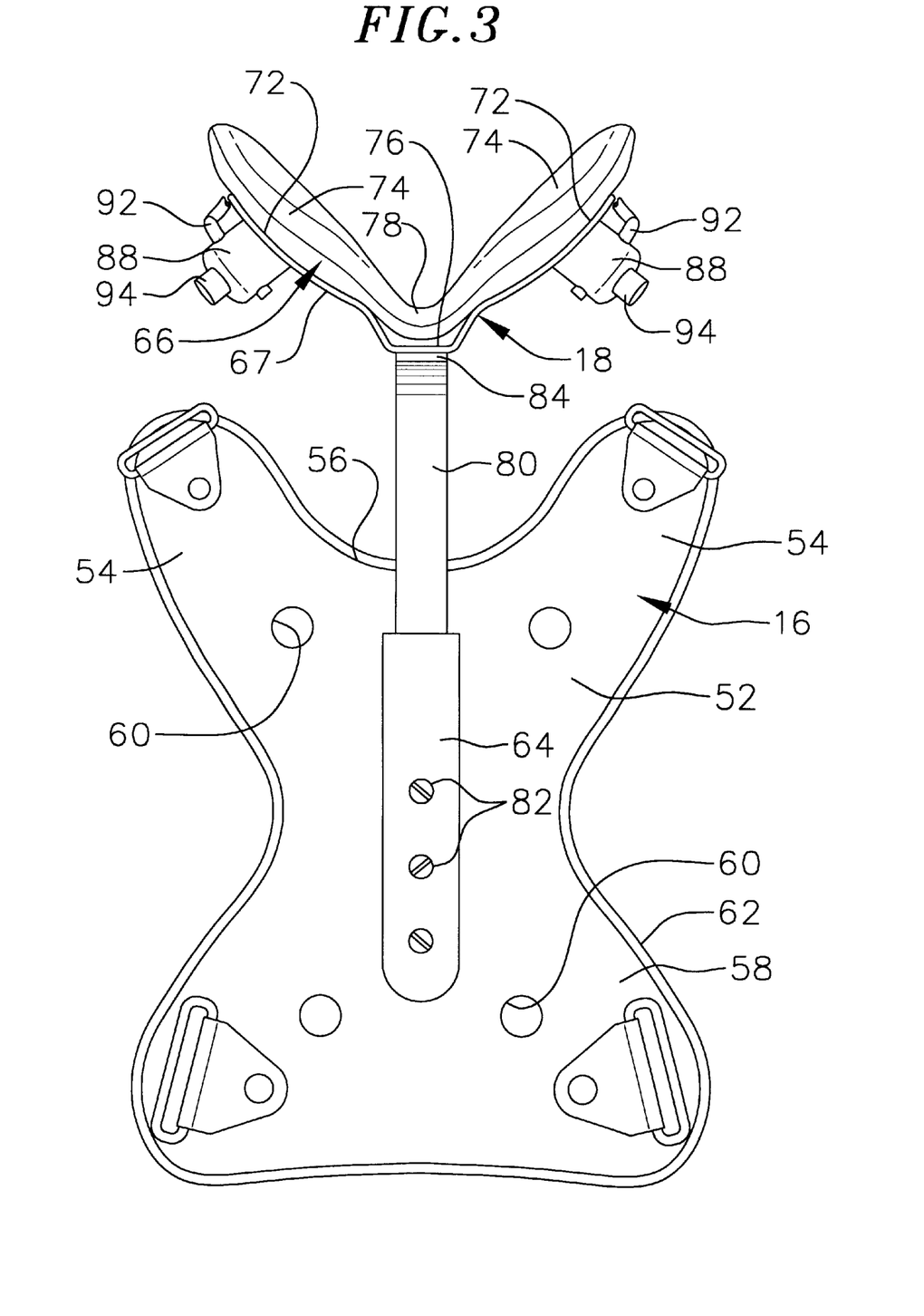
FIG. 3 is a front elevational view showing a chest plate and a chin support.

Referring to FIG. 3, the chest plate 16 comprises a thin semi-rigid shell 52 conforming to the anatomical shape of and overlying the patient's sternum. The chest plate has upwardly and outwardly projecting left and right upper portions 54 for overlying left and right portions of the patient's clavicle. The upper edge of the shell has a central U-shaped recess 56 for extending below the patient's neck. The opposite outer edges of the shell taper inwardly toward the middle of the shell and then diverge outwardly and downwardly toward an enlarged lower portion 58 of the shell that overlies the patient's midriff. The chest plate is preferably made from a thin walled, three dimensionally formed flexible plastic material such as polyethylene. Spaced apart holes 60 are left in the shell to enhance air circulation. The inside face of the shell is preferably covered by padding 62 comprising a layer of an open cell material with an outer layer of velour as used on the inside of the back plate.

A long narrow upright receptacle 64 extends along the center of the chest plate. This receptacle has an opening at its top and is of narrow profile made from the same technique as the receptacle on the back plate.

Figure 5:
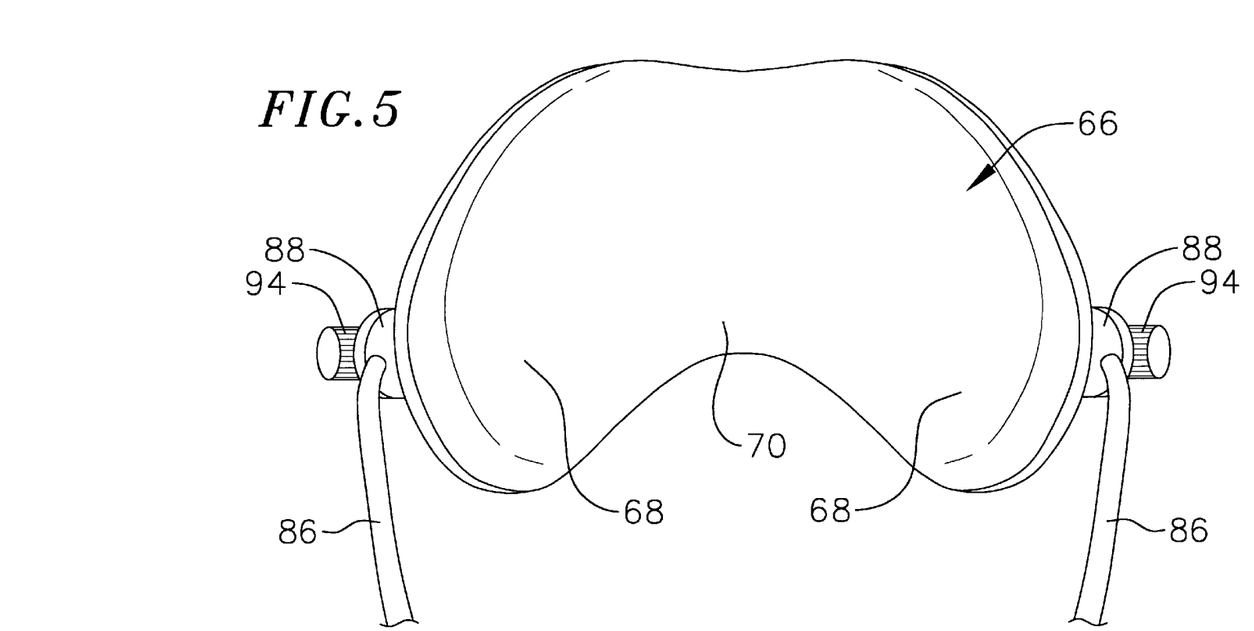
FIG. 5 is a top elevational view of the flexible chin support.

The chin support 18 comprises a flexible chin support pad 66 suspended inside a laterally extending generally V-shaped chin support member 67. The flexible chin support pad comprises an internal layer of open cell material contained within an outer two layer fabric piece comprising velour on the bottom side and a soft skin contacting layer of the upper side. The configuration of the flexible chin support pad 66 is best illustrated in FIG. 5 in which the chin support pad is widened at its outer regions 68 but narrowed along its central region 70. The bottom layer of velour is releasably secured to outer regions 72 of the U-shaped chin support member by cooperating friction fastener strips adhesively secured to the upwardly facing outer portions of the chin support member. Upwardly facing outer portions 74 of the flexible chin supported pad 66 contact the jaw regions of the patient during use.

The generally V-shaped chin support member 67 is a rigid piece made from hard plastic or metal. It is shaped as an upwardly opening member to conform to the anatomical configuration along opposite sides of the patient's jaw. A central region of the support member is recessed downwardly by an abrupt recess 76 projecting away from the region below the patient's chin. Direct pressure contact is avoided and no rigid support is provided by the support member against the lower portion of the patient's chin, as a result of the recessed central portion of the chin support member being spaced well below the bottom of the patient's chin. The previously mentioned friction fasteners for securing the flexible chin support pad to the inside of the chin support member provide a means for adjustably suspending the flexible chin supporting pad within the chin support member, so that the flexible chin support pad can be in contact with the lower portion of patient's chin, but provides the sole means of support for the underside of the patient's chin bone. The releasable attachment means at the outer regions 72 of the chin support member provide a means for adjustably and releasably securing the flexible chin support pad in contact with the sides of the patient's jaws and the underside of the patient's chin to match the patient's anatomical configurations in that area. This means of suspension of the chin support pad 66 ensures that a central portion 78 of the flexible pad may be able to flex downwardly into the recessed central region 76 of the chin support member 67 without making physical contact with the rigid portion of the member.

An upright rigid metal bar 80 extends vertically below the chin support member 67. The support bar 80 fits into the long narrow opening inside the receptacle 64 at the front of the chest plate 52. Spaced apart threaded holes (not shown) in the lower portion of the bar are aligned with holes in the receptacle when adjusting the chin support pad upwardly or downwardly to the desired elevation. Fasteners 82 are threaded into the holes of the bar for securing the bar in a fixed position on the chest plate. An upper portion 84 of the upright bar is bent at a right angle, and the lower central recessed portion 76 of the chin support member has a flat surface which rests on this right angle bend. Fasteners rigidly affix the recessed lower portion of the chin support member to the right angle bend at the top of the upright bar. The support ban 80 can be made with a large donut-shaped opening (not shown) for tracheotomy access.

Figure 4:
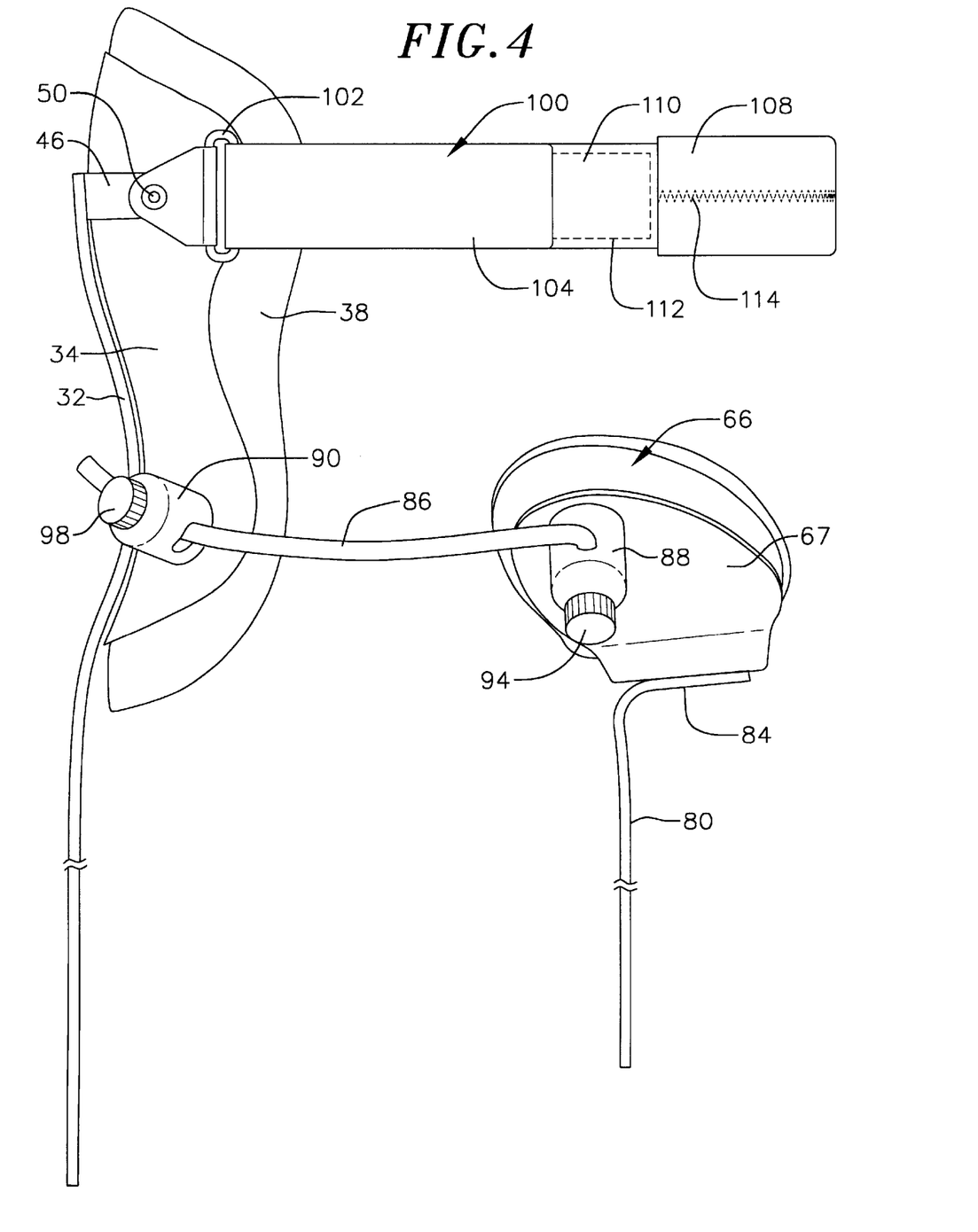
FIG. 4 is a side elevational view showing the occipital support and the chin support secured together as part of a rigid frame structure by one of two lateral support bars.

The occipital support and chin support are secured together as a rigid frame structure by left and right lateral frame support rods 86. These rods are preferably made of hard plastic and are generally circular in cross-section, approximately one-fourth inch in diameter. The anterior and posterior ends of the rods are preferably releasably secured to the underside of the chin support member 67 and to the outer sides of the occipital support shell 34. The anterior ends of the rods are preferably releasably secured to corresponding anterior posts 88 rigidly secured to and projecting downwardly from lower outer regions of the chin support member. Similarly, the posterior ends of the rods are preferably releasably secured to rear posts 90 rigidly secured to and projecting outwardly from the lower outer portions of the occipital support. The releasable attachment of the anterior ends of the bars preferably comprises bending a front end 92 of each bar at a right angle and extending it through a threaded opening in each corresponding anterior post. Cap screws 94 in the anterior posts 88 are tightened to securely fasten each right angle bend to the post and thereby to the outer portion of the chin support member. The anterior posts are preferably made of hard plastic. These releasable attachments of the front ends of the bars 86 are for the purpose of allowing these bars to be removed so they can be bent into a desired anatomical configuration around the sides of the patient's neck region. The posterior ends 96 of the rods 86 extend through corresponding openings in the rear posts 90. Rear cap screws 98 are tightened to rigidly hold the rods in place on the occipital support. The posterior ends of the bars 86 extend through the rear posts along a front-to-rear alignment so that the relative distance between each anterior post 88 and its corresponding rear post 90 can be adjusted to thereby adjust the effective length of each rod along each side of the patient independently. The rods are axially rigid and are preferably bendable sufficiently to be shaped to the anatomical contours along side the patient's neck and lower jaw region.

Figure 6:
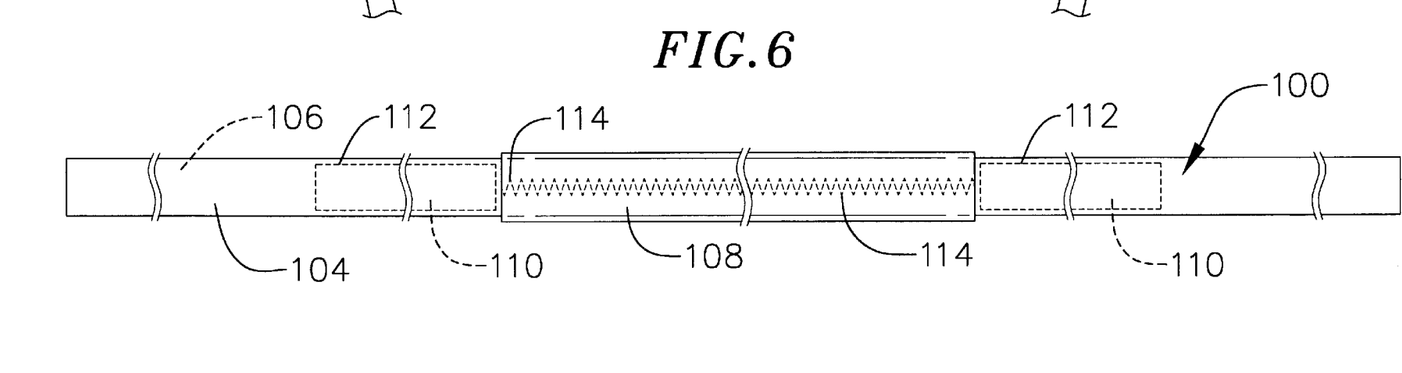
FIG. 6 is an elevational view showing detailed construction of the forehead strap.

An elongated flexible forehead strap 100 is releasably secured around the patient's head. The ends of the forehead strap are releasably secured to opposite outer portions of the lateral occipital support bar 46. The forehead strap is adjustable in length so that it can extend around the patient's forehead so the patient's head can be tightly held against the padded front side of the occipital support 14. Opposite ends of the forehead strap are releasably secured to cooperating ring fasteners 102 affixed to the lateral support bar by the rivets 50. FIG. 6 best illustrates detailed construction of the forehead strap which is preferably made from a nylon strip 104 about two feet in length and about one inch wide. A strip 106 of friction fastener material of the velour or pile type extends along the entire rear side of the forehead strip (the side shown in FIG. 6). An elongated skin adhesion layer 108 extends along a central region of the forehead strap preferably about six to eight inches in length. On the rear side of the forehead strap, short strips 110 of a friction fastener material of the hook type extend adjacent the ends of the skin adhesion layer for about three to four inches on each side. These strips 110 are secured to the forehead strap by stitching 112.

The skin adhesion layer 108 preferably comprises a layer of non-skid material capable of frictionally adhering to (but easily removable from contact with) the patient's skin for long periods of time without detrimental effects to the patient's skin or comfort during use. The skin adhesion layer is preferably made from a layer of thermoplastic silicone gel or similar medical grade material having a somewhat tacky surface providing frictional contact with the skin when held in tight contact with the skin. The skin adhesion material is an inert material which can be worn against the skin for long periods of time without causing skin irritations or discomfort. The presently preferred material is a silicone gel such as Walco Silicone V-1082 HiPro Clear available as a gel mixed with a promoter and/or a tri-block polymer with medical grade mineral oil by Silipos. The finished layer of skin adhesion material is wrapped around the front and rear sides of the nylon strip 104 and then fastened along its length by stitching 114. Alternatively, the gel can be poured onto a flexible layer of a reinforcing fabric such as Tricot, nylon or other similar flexible fabric material such as a woven fibrous material which can absorb the gel material and maintain it as a thin layer of uniform thickness on its surface. In the illustrated embodiment, the gel layer is reinforced by the nylon strip 104 with has a tensile strength greatly exceeding that of the film of gel material which is wrapped around the reinforcing layer. The reinforcement avoids tearing and more easily fastens the gel material to the forehead strap.

In using the forehead strap 100, the free ends of the strap are each threaded through corresponding ring fasteners 102 on the occipital support and then folded back for cooperating releasable attachment to the friction fastener sections 110 adjacent the skin adhesion layer. This provides a means of adjusting the length of the forehead strap to match the contour of the patient's head and to firmly secure the patient's head against the occipital support 14 in a manner similar to a halo type means of support.

In use, the forehead strap 100 is held around the patient's head by adjusting its pressure around the head by appropriate adjustments of the friction fasteners. This holds the skin adhesion layer 108 in non-slip contact with the patient's skin along the forehead.

The chin support pad 66 suspends the chin inside the chin support member 67 so that the chin bone does not contact a rigid section of the chin support. A continuous means of rigid support to the patient's chin bone has been found to be undesirable. The applied pressure can break down the bone. The chin support pad of this invention can be used up for making firm lateral means of pressure contact with the sides of the patient's jaw region (via the lateral means of support at 72 from the chin support member) without applying pressure to the chin bone. The recessed region 76 along the center of the chin support member 67 provides an open space absent any means of applying rigid pressure contact to the underside of the patient's chin bone. The desired amount of pressure under the chin and along the sides of the jaws can be set by adjusting the padded flexible chin support in the regions 74 and 78 via the friction fastener adjustments to the regions 72 of the chin support member 67.

The lateral support rods 86 provide a rigid connection between the chin support and the occipital support. With the support rods locked in place, a rigid box frame structure is formed around the patient's neck and jaw regions to cooperate with the front and rear immobilization provided by the chin support and the occipital support. The rigid frame structure prevents the patient's chin from sliding down and also enhances rigidity of the entire orthosis, which provides more effective immobilization of the patient's head. The semi-rigid rods are preferably made of polyethylene or nylon which facilitate contouring to fit the contour the neck. The rods can be shaped to this contour without special tools. However, the rods are rigid axially to provide the desired level of rigidity when acting as a frame structure in cooperation with the attachments to the chin support and occipital support.

The forehead strap 100 cooperates with the rigid frame structure to provide an improved means of immobilizing the patient's head. With the chin support and lateral support rods locked in place, the forehead strap enhances immobilization by providing a means of resisting bending motion of the neck and by providing rotational stability not present in the absence of the forehead strap.

In addition, the forehead strap provides a means of adhesion to the patient's head at 108 for temporarily immobilizing it while properly adjusting the chin support. That is, the chin support can be raised or lowered while the forehead strap holds the patient's head against the accepted support. The chin support also can be lowered temporarily to assist the patient during eating while the forehead strap provides sufficient skin adhesion along the forehead for temporarily immobilizing the patient's head.

What is claimed is:

1. In a cervical thoracic orthosis comprising a chest plate for overlying a patient's chest, and a back plate for overlying a patient's back, an occipital support rigidly secured to the back plate for supporting the occipital and neck region of the patient, a chin support secured to the chest plate for supporting the chin and lower jaw region of the patient's head, and fasteners for securing the chest plate and the back plate in a fixed position around the patient's upper torso for holding the occipital support and the chin support in fixed positions, the improvement comprising axially rigid but bendable lateral support bars fastened between and cooperating with the occipital support and the chin support to form a rigid frame structure surrounding the sides of the patient's neck region and the patient's jaw, and a flexible forehead strap secured to the occipital support and adjustable for fastening around the patient's forehead to provide sufficient support to preclude movement of the patient's head, the forehead strap made from a skin adhesion material to enhance frictional contact with the patient's head and prevent slippage sufficiently for resisting movement of the patient's head even in the temporary absence of the chin support.

2. The improvement according to claim 1 in which the chin support comprises a flexible pressure-relieving chin support suspended inside a rigid chin support member; and in which the chin support member includes a front center recess, in which the flexible chin support is suspended to apply supporting pressure to the sides of the patient's jaw while the flexible chin support provides the sole means of support for the chin above the recessed region of the chin support member.

3. The improvement according to claim 2 including friction fasteners between sides of the flexible chin support and cooperating inside portions of the chin support member adjacent the jaw regions of the patient's head to suspend the flexible chin support within the chin support member in the absence of rigid contact with the front central recessed region of the chin support member.

4. The improvement according to claim 1 in which the forehead strap comprises a layer of non-skid material.

5. The improvement according to claim 4 in which the non-skid layer is secured to a flexible reinforcing strap having a substantially greater tensile strength than the skin adhesion layer.

6. The improvement according to claim 5 in which the non-skid layer is made from a silicone gel material or a medical grade tri block polymer.

7. The improvement according to claim 1 in which the lateral support bars are made of plastic material which is bendable laterally to conform to the contour around the patient's neck region but is sufficiently rigid axially to provide said rigid frame structure.

8. The improvement according to claim 7 including anterior releasable attachable devices on lower side portions of the chin support member, and posterior releasable attachment devices on lower side portions of the occipital support, the lateral support bars each releasably secured to a cooperating pair of anterior and posterior attachment devices for adjusting the length of each lateral support bar along the sides of the orthosis.

9. In a cervical thoracic orthosis comprising a chest plate for overlying a patient's chest, and a back plate for overlying a patient's back, an occipital support rigidly secured to the back plate for supporting the occipital and neck region of the patient, a chin support secured to the chest plate for supporting the chin and lower jaw region of the patient's head, and fasteners for securing the chest plate and the back plate in a fixed position around the patient's upper torso for holding the occipital support and the chin support in fixed positions, the improvement comprising axially rigid but bendable lateral support bars fastened between and cooperating with the occipital support and the chin support to form a rigid frame structure surrounding the sides of the patient's neck region and the patient's jaw, and a flexible forehead strap secured to the occipital support and adjustable for fastening around the patient's forehead to provide sufficient support to preclude movement of the patient's head, the forehead strap made from a skin adhesion material to enhance frictional contact with the patient's head and prevent slippage sufficiently for resisting movement of the patient's head even in the temporary absence of the chin support, in which the chin support member includes a front central recess, in which the chin support comprises a flexible pressure-relieving chin support suspended inside a rigid chin support member to apply supporting pressure to the sides of the patient's jaw while the flexible chin support provides the sole means of support for the chin above a recessed region of the chin support member.

10. The improvement according to claim 9 including friction fasteners between sides of the flexible chin support and cooperating inside portions of the chin support member adjacent the jaw regions of the patient's head to suspend the flexible chin support within the chin support member in the absence of rigid contact with the front central recessed region of the chin support member.

11. The improvement according to claim 9 in which the forehead strap comprises a layer of non-skid plastic material.

12. The improvement according to claim 11 in which the non-skid skid layer is secured to a flexible reinforcing strap having a substantially greater tensile strength than the skin adhesion layer.

13. The improvement according to claim 12 in which the non-skid skid layer is made from a skin-adhering material.

14. The improvement according to claim 9 in which the lateral support bars are made of plastic material which is bendable laterally to conform to the contour around the patient's neck region but is sufficiently rigid axially to provide said rigid frame structure.

15. The improvement according to claim 14 including anterior releasable attachable devices on lower side portions of the chin support member, and posterior releasable attachment devices on lower side portions of the occipital support, the lateral support bars each releasably secured to a cooperating pair of anterior and posterior attachment devices for adjusting the length of each lateral support bar along the sides of the orthosis.

16. In a cervical thoracic orthosis comprising a chest plate for overlying a patient's chest, and a back plate for overlying a patient's back, an occipital support rigidly secured to the back plate for supporting the occipital and neck region of the patient, a chin support secured to the chest plate for supporting the chin and lower jaw region of the patient's head, and fastened for securing the chest plate and the back plate in a fixed position around the patient's upper torso for holding the occipital support and the chin support in fixed positions, the improvement comprising axially rigid but bendable lateral support bars fastened between and cooperating with the occipital support and the chin support to form a rigid frame structure surrounding the sides of the patient's neck region and the patient's jaw, and a flexible forehead strap secured to the occipital support and adjustable for fastening around the patient's forehead to provide sufficient support to preclude movement of the patient's head, in which the chin support comprises a flexible pressure-relieving chin support pad releasably suspended inside a rigid chin support member which includes rigid side portions and a front central recess between the side portions and projecting downwardly below the side portions, in which the flexible chin support pad is releasably secured to the rigid side portions, with a lower central portion of the chin support pad spaced above the front central recess, the chin support pad thereby suspended so as to apply supporting pressure to the sides of the patient's jaw while the lower central portion of the flexible chin support pad provides the sole means of support for the chin spaced above the recessed region of the chin support member.

17. In a cervical thoracic orthosis comprising a chest plate for overlying a patient's chest, and a back plate for overlying a patient's back, an occipital support rigidly secured to the back plate for supporting the occipital and neck region of the patient, a chin support secured to the chest plate for supporting the chin and lower jaw region of the patient's head, and fasteners for securing the chest plate and the back plate in a fixed position around the patient's upper torso for holding the occipital support and the chin support in fixed positions, the improvement comprising lateral support bars fastened between and cooperating with the occipital support and the chin support to form a frame structure surrounding the sides of the patient's neck region and the patient's jaw, and a flexible forehead strap secured to the occipital support and adjustable for fastening around the patient's forehead to provide sufficient support to preclude movement of the patient's head, the forehead strap made from a skin adhesion material to enhance frictional contact with the patient's head and prevent slippage sufficiently for resisting movement of the patient's head even in the temporary absence of the chin support.

18. The improvement according to claim 17 in which the forehead strap comprises a layer of non-skid material.

19. The improvement according to claim 18 in which the non-skid layer is secured to a flexible reinforcing strap having a substantially greater tensile strength than the skin adhesion layer.

20. The improvement according to claim 19 in which the non-skid layer is made from a silicone gel material or a medical grade tri block polymer.

\* \* \* \* \*